(12) United States Patent
Di Girolamo et al.

(10) Patent No.: US 9,233,352 B2
(45) Date of Patent: Jan. 12, 2016

(54) MODIFIED TUBULAR REACTOR AND PROCESS FOR EFFECTING CATALYTIC REACTIONS INVOLVING THERMAL EXCHANGES IN WHICH IT IS USED

(75) Inventors: Marco Di Girolamo, San Donato Milanese (IT); Maura Brianti, Busto Arsizio (IT); Massimo Conte, Peschiera Borromeo (IT)

(73) Assignee: SAIPEM S.p.A., San Donato Milanese (IT)

(*) Notice: Subject to any disclaimer, the term of this patent is extended or adjusted under 35 U.S.C. 154(b) by 982 days.

(21) Appl. No.: 12/673,317

(22) PCT Filed: Aug. 7, 2008

(86) PCT No.: PCT/EP2008/006693
§ 371 (c)(1),
(2), (4) Date: Jul. 16, 2010

(87) PCT Pub. No.: WO2009/021736
PCT Pub. Date: Feb. 19, 2009

(65) Prior Publication Data
US 2011/0213186 A1    Sep. 1, 2011

(30) Foreign Application Priority Data
Aug. 14, 2007    (IT) .............................. MI2007A1675

(51) Int. Cl.
*C07C 41/06*    (2006.01)
*B01J 8/06*    (2006.01)
*B01J 8/00*    (2006.01)
*C07C 2/08*    (2006.01)
*C10G 3/00*    (2006.01)

(52) U.S. Cl.
CPC *B01J 8/067* (2013.01); *B01J 8/003* (2013.01); *B01J 8/008* (2013.01); *B01J 8/065* (2013.01); *C07C 2/08* (2013.01); *C07C 41/06* (2013.01); *C10G 3/42* (2013.01); *B01J 2208/00212* (2013.01); *B01J 2208/00849* (2013.01); *B01J 2208/00884* (2013.01); *C10G 2400/02* (2013.01)

(58) Field of Classification Search
None
See application file for complete search history.

(56) References Cited

U.S. PATENT DOCUMENTS 2,631,159 A  *  3/1953  Keith ............................ 518/706
4,570,026 A       2/1986  Keyworth et al.
(Continued)

FOREIGN PATENT DOCUMENTS

DE    100 47 693         4/2002
DE    10047693 A1  *  4/2002  ................ B01J 8/00
(Continued)

*Primary Examiner* — Rosalynd Keys
(74) *Attorney, Agent, or Firm* — Oblon, McClelland, Maier & Neustadt, L.L.P.

(57) ABSTRACT

A tubular reactor is described, for catalytic reactions involving thermal exchanges, in particular for etherification reactions between branched olefins and linear alcohol, for dimerization reactions of branched olefins or cracking reactions, essentially consisting of a vertical tube-bundle exchanger whose tubes contain catalyst, having inlet and outlet nozzles for each passage side of the reagents, catalyst and thermal exchange liquid, characterized in that it has one or more metallic supports situated outside the lower tube plate in the lower part of the reactor for sustaining the catalyst so that the same catalyst is contained not only in the tubes of the tube-bundle but also in said lower part outside the lower tube plate and also in the upper part outside the upper tube plate.

44 Claims, 6 Drawing Sheets

(56) References Cited

U.S. PATENT DOCUMENTS

| | | | |
|---|---|---|---|
| 4,929,798 A * | 5/1990 | de Lasa | 585/402 |
| 5,292,904 A * | 3/1994 | Sawada et al. | 549/534 |
| 5,417,938 A * | 5/1995 | Shelden et al. | 422/601 |
| 2002/0002316 A1 | 1/2002 | Girolamo et al. | |
| 2004/0250868 A1 | 12/2004 | Yada et al. | |
| 2005/0028874 A1 | 2/2005 | Olbert et al. | |
| 2007/0122322 A1* | 5/2007 | Te Raa et al. | 422/197 |
| 2007/0203369 A1* | 8/2007 | Praefke et al. | 568/690 |
| 2008/0058569 A1* | 3/2008 | Winterberg et al. | 585/639 |
| 2008/0216915 A1 | 9/2008 | Yada et al. | |
| 2008/0234522 A1 | 9/2008 | Yada et al. | |
| 2008/0253943 A1 | 10/2008 | Yada et al. | |

FOREIGN PATENT DOCUMENTS

| | | |
|---|---|---|
| EP | 1 466 883 | 10/2004 |
| WO | 2007 045574 | 4/2007 |

* cited by examiner

MODIFIED TUBULAR REACTOR AND PROCESS FOR EFFECTING CATALYTIC REACTIONS INVOLVING THERMAL EXCHANGES IN WHICH IT IS USED

CROSS REFERENCE TO RELATED APPLICATION

This application is a 371 of PCT/EP 2008/006693, filed on Aug. 7, 2008, and claims priority to Italian Patent Application No. MI2007A001675, filed on Aug. 14, 2007.

The present invention relates to a modified tubular reactor and the process for its use in catalytic reactions involving thermal exchanges carried out in liquid and/or vapour phase.

Tubular reactors generally consist of vertical tube-bundle exchangers, in which the catalyst is kept in the tubes by means of metallic supports whereas the fluid used for releasing or removing heat, flows in the shell side.

This type of reactor is successfully used in both endothermic and exothermic reactions.

A typical example of an endothermic reaction is the cracking reaction of MTBE (methyl tert butyl ether), used for the production of high-purity isobutene, in which the reaction heat is supplied by circulating hot oil or steam in the shell side.

Tubular reactors however are mainly used in exothermic reactions and typical examples of application are the etherification and/or selective dimerization of branched olefins (iso-olefins) contained in $C_4$ and $C_5$ hydrocarbon cuts.

Through these reactions, it is in fact possible to convert isobutene and isoamlyenes (2-methyl-1-butene and 2-methyl-2-butene), which are the most reactive olefins present in $C_4$ and $C_5$ streams, into high-octane compounds such as ethers of the MTBE, ETBE (ethyl tert butyl ether), TAME (methyl tert amyl ether), TAEE (ethyl tert amyl ether) and/or hydrocarbon streams such as iso-octene (cut containing at least 80% of $C_8$ hydrocarbons).

Due to the high octane characteristics (both Research Octane Number (RON) and Motor Octane Number (MON)), the low volatility, the absence of the most harmful products for the environment (sulfur, aromatic products, benzene, etc.), all these compounds (hydrocarbons and/or oxygenated compounds) fall into the category of compositions which are extremely interesting for obtaining gasolines more compatible with present environmental demands.

In order to respond to the ever-increasing request in future gasolines for compounds having these characteristics, there is therefore the necessity of improving their production processes also with the use of simpler and more functional reactors.

All of these compounds are synthesized in substantially similar plants as the reactors (tubular and adiabatic) and catalysts (ion exchange acid resins) are practically the same for both etherification and dimerization reactions of branched olefins.

Whereas in the case of etherification, it is sufficient to react the iso-olefin with a linear alcohol (preferably methanol and/or ethanol), in the case of dimerization, in order to succeed in obtaining a high-quality product (content of dimers higher than 80% weight), it is necessary to use moderate quantities of oxygenated compounds (ethers and/or alcohol) capable of moderating the activity of the catalyst and therefore control the reaction rate obtaining the desired selectivity to dimers.

Oxygenated compounds which can be used in the case of $C_4$ streams are:

primary alcohol in a sub-stoichiometric quantity with respect to the isobutene fed in the feedstock (IT-M195/A001140 of 1 Jun. 1995);

primary alcohol and/or alkyl ether in a substoichiometric quantity with respect to the isobutene fed in the feedstock (IT-M197/A001129 of 15 May 1997);

tertiary alcohol and/or alkyl ether and/or primary alcohol in a sub-stoichiometric quantity with respect to the isobutene fed in the feedstock (IT-M199/A001765 of 5 Aug. 1999);

tertiary alcohol (such as tertbutyl alcohol—TBA) in a sub-stoichiometric quantity with respect to the isobutene fed in the feedstock (IT-M194/A001089 of 27 May 1994).

Hydrocarbon streams, used in the etherification and/or dimerization reaction, mainly containing isobutane, isobutene, n-butane, n-butenes, isoamylenes and saturated and olefinic $C_5$ hydrocarbons.

Although a wide variety of sources is available for providing these streams, the most common relate to those deriving from dehydrogenation processes of iso-paraffins, FCC units, steam cracking units or processes for pure isobutene production, such as the TBA dehydration or cracking of MTBE or ETBE; these streams differ from each other in the content of branched and linear olefins. The branched olefin is mainly converted in the reaction area, part of the $C_4$-$C_5$ olefins present, however, can also be converted to useful product.

The use of tubular reactors is fundamental for obtaining the high selectivities which, by using the minimum quantity of catalyst with the same performances, are able to remove the reaction heat, limit the formation of by-products in the case of etherification and avoid, in the case of dimerization, the initiation of oligomerization and polymerization reactions of olefins which are favoured by high temperatures.

Figure 1:
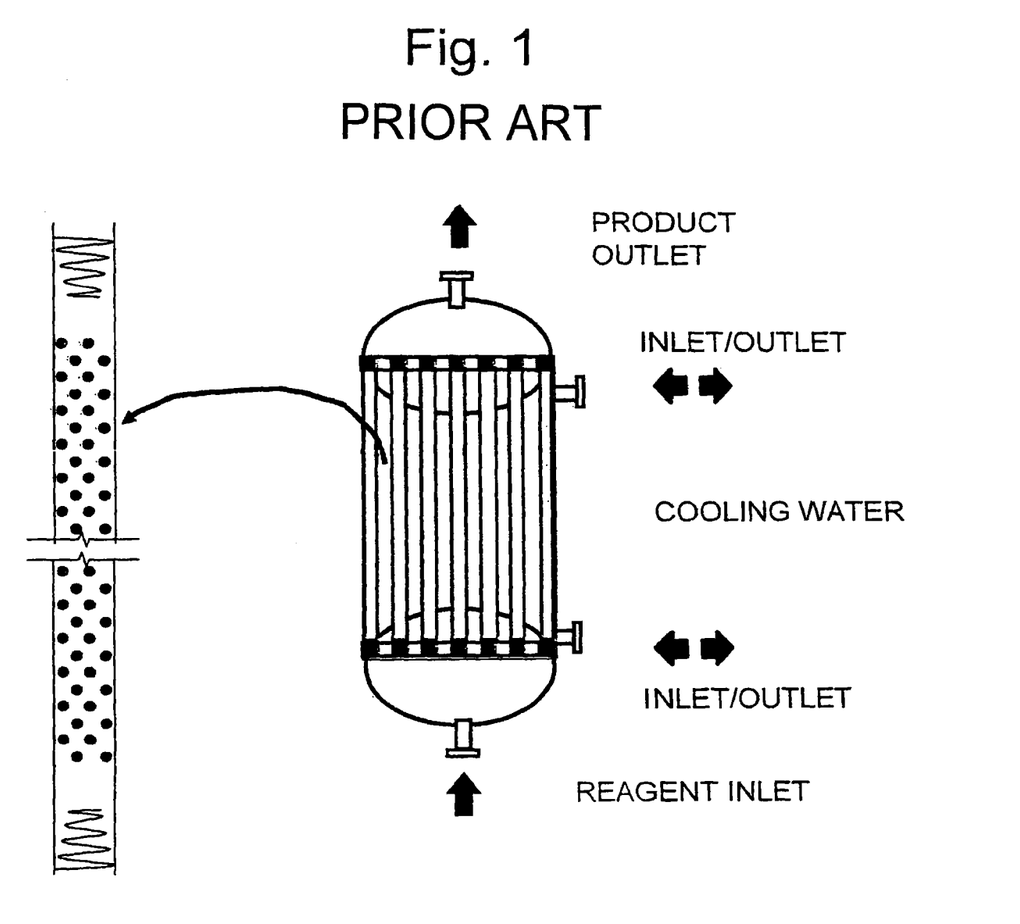
FIG. 1 shows a reactor where the catalyst is situated in the tubes.
Figure 2:
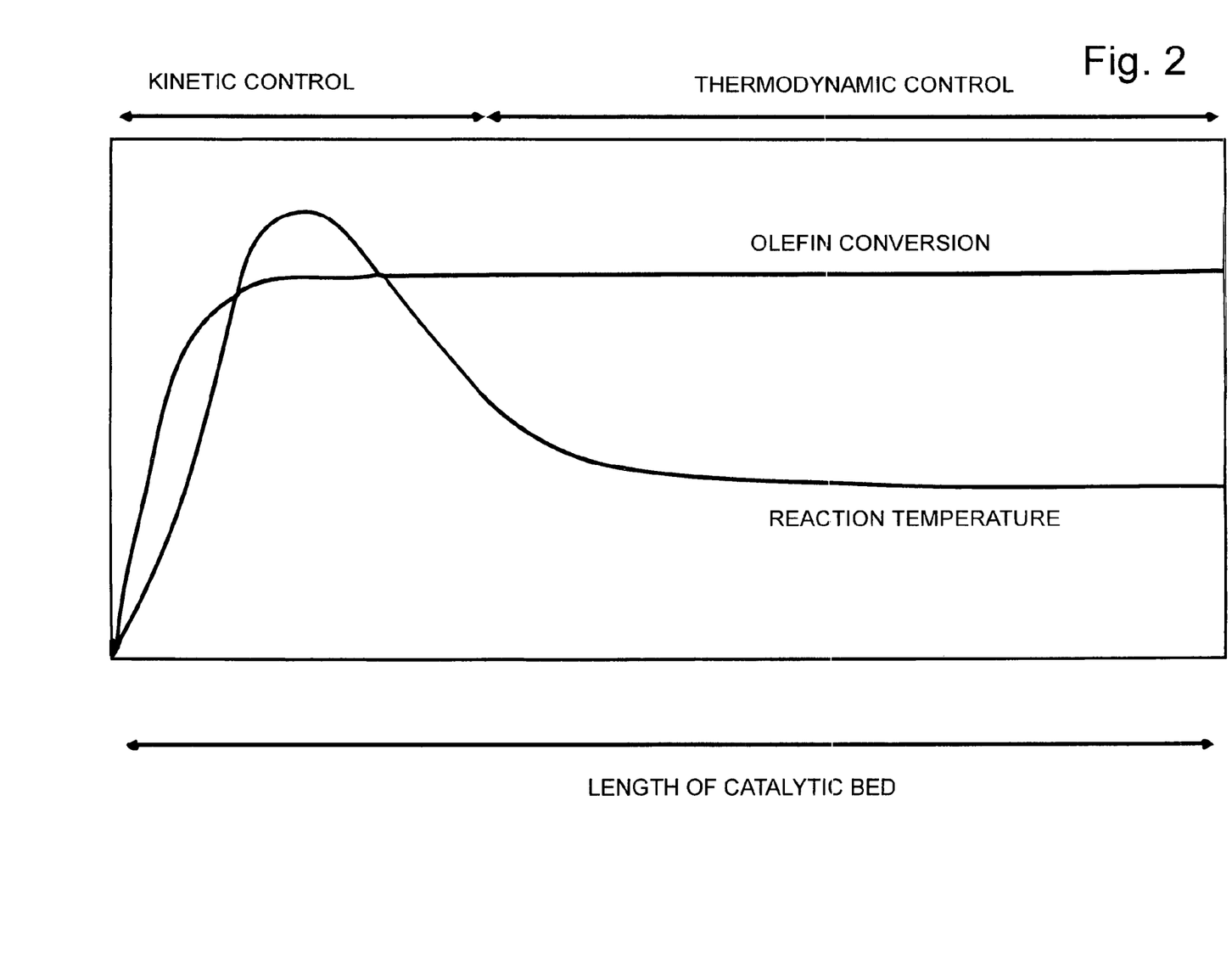
FIG. 2 shows that the temperature of he reactor is high in the first part of the catalytic bed to ensure kinetic support for the reaction and as low as possible at the reactor outlet, in order to maximize the thermodynamic conversion and minimize the production of by-products.

In these reactors, as shown in FIG. 1, the catalyst is situated in the tubes, whereas the tempered water flows in the shell side, to remove the reaction heat and consequently obtain an optimum temperature profile for an exothermic reaction; in this case, in fact, the temperature, as indicated in FIG. 2, is high in the first part of the catalytic bed to ensure kinetic support for the reaction and as low as possible at the reactor outlet, in order to maximize the thermodynamic conversion and minimize the production of by-products.

This particular thermal profile also gives to the tubular reactor greater resistance to poisons, because only the initial part of the catalytic bed is effectively involved in the synthesis, whereas the remaining part (used for achieving the equilibrium conversion) practically acts as a catalyst reserve.

In spite of the fact, therefore, that only a part of the catalyst is actually used, this reactor uses, with the same performances, a much lower quantity of catalyst than that of an adiabatic reactor.

In the case of deactivation of the catalyst, it is also possible to use the tempered water for giving thermal support to the reaction.

The tempered water can flow either in co-current or countercurrent with respect to the process fluid, in relation to the quantity of heat to be removed, and it is recirculated by means of a pump after being cooled to the desired temperature in an external exchanger.

This reactor has a great operating flexibility because is possible to control the internal temperature and consequently the reaction rate by modifying both the inlet temperature of the reagents and the temperature and flow-rate of the tempered water.

The process fluid flows upwardly through the tubes to limit packing phenomena of the catalyst and significantly reduce pressure drops but occasionally it can also be fed from the top downwards.

The behaviour of this reactor is the same both in the case of very concentrated and also extremely diluted feed-stocks and consequently the tubular reactor can indifferently treat any type of feedstock; for this reason it is normally used as front-end reactor (where most of the conversion is realized) in etherification and/or dimerization plants in both the first and also in a possible second stage.

A wide variety of solid acid catalysts can be used in this type of reactor, but styrene-divinylbenzene polymeric resins having sulfonic groups as catalytic centres such as, for example, Amberlyst 15 and 35 in the case of etherification and dimerization, and silicon and/or aluminum oxides in the case of cracking reactions of alkyl ethers, are preferred.

A wide range of operating conditions can be used; the desired reactions can be carried out in vapour phase (preferred condition for cracking reactions), in liquid-vapour phase or in liquid phase (preferred condition for etherification and dimerization reactions).

The pressure is preferably superatmospheric and generally below 5 MPa, more preferably between 0.2-3.0 MPa. The temperature varies in relation to the type of reaction and generally below 300° C. for cracking and preferably from 30 to 120° C. for etherification and dimerization reactions.

These reactors can normally be made of carbon steel or stainless steel but it is also possible to use a combination of the two materials; for example it is possible to produce a reactor using stainless steel only for the tubes.

This type of reactor is obviously more expensive than a simple adiabatic reactor, but it has so many operational advantages that it is just as competitive.

The main limit of this type of reactor, on the other hand, consists in the fact that the loading and unloading procedure of the catalyst is extremely lengthy and onerous; the catalyst is in fact kept inside the tubes, whose number can even reach various thousands, with the use of particular metallic supports, mesh-windings and springs, situated at both ends of each tube (as shown in FIG. 1) which must be installed and removed for its load and unload.

A suitably modified tubular reactor has now been found, without metallic supporting devices of the catalyst in the tubes, which is much more flexible and efficient and easier to manage, with respect to the loading and unloading operations of the catalyst.

The tubular reactor, object of the present invention, for catalytic reactions involving thermal exchanges, essentially consists of a vertical tube-bundle exchanger whose tubes contain catalyst, having inlet and outlet nozzles for each passage side of the reagents, catalyst and thermal exchange liquid, characterized in that it has one or more metallic supports situated outside the lower tube plate in the lower part of the reactor for sustaining the catalyst so that the same catalyst is contained not only in the tubes of the tube-bundle but also in said lower part outside the lower tube plate and also in the upper part outside the upper tube plate.

In particular, in the upper part, the height of catalyst is preferably higher than 10 mm and more preferably higher than 50 mm with respect to the upper tube plate.

The metallic support is preferably positioned close to or on the lower inlet/outlet nozzle of the reactor.

A feeding distributor, which preferably comprises a series of vertical and/or side holes, can be also present in communication with the lower inlet/outlet nozzle of the reactor.

The distributor should be positioned at a distance from the tube plate preferably greater than 10 mm, more preferably greater than 50 mm. A flow deflector, possibly partially perforated, can be present above the distributor.

The reactor can have several feeding nozzles, preferably two or four, equidistant from the vertical axis of the reactor, each in communication with a feeding distributor, above which a flow deflector, preferably perforated, can be positioned.

Said flow deflector positioned above each distributor can be tilted: it is preferably a perforated plate with a tilt angle ranging from 5 to 80°, more preferably from 10 to 70°.

A further central feeding nozzle of the reagent can be present at the bottom of the reactor.

The reactor according to the invention can be made of carbon steel or stainless steel or using a combination of the two materials.

A second object of the present invention relates to the process for effecting catalytic reactions, both exothermic and endothermic, carried out in liquid or vapour phase, involving thermal exchanges, which is characterized in that it uses the reactor according to the invention.

The process for effecting catalytic reactions, preferably exothermic, in liquid phase, can be characterized by the following further essential aspects:
  the process fluid preferably flows upwards;
  the cooling fluid flows in the shell side in co-current or countercurrent with respect to the reagents in relation to the quantity of heat to be exchanged;
  the cooling fluid leaving the reactor is cool down to the desired temperature in a suitable external item before being re-circulating into the reactor.

The catalyst preferably consists of styrene-divinylbenzene polymeric resins having sulfonic groups as functional centres.

The linear rates inside the reactor are preferably lower than 4.5 cm/sec.

The cooling liquid is preferably water.

The minimum height of catalyst above the upper tube plate is preferably at least 10 mm, and more preferably at least 50 mm.

The catalytic reactions involving thermal exchanges are preferably etherification reactions between branched olefins and linear alcohol or dimerization reactions of branched olefins.

The process for the etherification reaction between branched olefins and linear alcohol is preferably effected at temperatures ranging from 30 to 120° C. and at pressures ranging from 0.2 to 3.0 MPa.

The linear alcohol is preferably selected from methanol and/or ethanol.

The branched olefin has a number of carbon atoms preferably ranging from 4 to 7.

The process for the dimerization reaction of branched olefins is preferably effected at temperatures ranging from 30 to 120° C. and pressures ranging from 0.2 to 3.0 MPa.

The branched olefin has a number of carbon atoms preferably ranging from 4 to 7.

The dimerization reaction is preferably carried out in the presence of linear alcohols and/or alkyl ether and/or branched alcohols.

The alkyl ether is preferably selected from MTBE, ETBE, MSBE (methyl sec-butyl ether), ESBE (ethyl sec-butyl ether), TAME, TAEE or mixtures thereof.

The branched alcohol has a number of carbon atoms preferably ranging from 4 to 7.

The linear alcohol is preferably selected from methanol and/or ethanol.

Other possible olefins present in the feedstock can also react to form high-octane products for both etherification and dimerization reactions.

The etherification and dimerization reactions of branched olefins can also be carried out contemporaneously.

The process for effecting catalytic reactions, preferably endothermic, in vapour phase can be characterized by the following further essential aspects:
 the process fluid preferably flows downwards;
 the heater fluid flows in the shell side in co-current or countercurrent with respect to the reagents in relation to the quantity of heat to be exchanged;
 the heater fluid leaving the reactor is reated to the desired temperature in a suitable external item (oven or boiler) before being re-introduced into the reactor.

The heater fluid is preferably steam or hot oil.

The endothermic catalytic reactions involving thermal exchanges are preferably cracking reactions of ethers, preferably selected from MTBE, ETBE, MSBE, ESBE, TAME, TAEE or mixtures thereof, or of branched alcohols, preferably with a number of carbon atoms ranging from 3 to 7, the mast preferable is TBA.

For these cracking reactions, the catalyst preferably substantially consists of silicon and/or aluminum oxides.

The minimum height of catalyst above the upper tube plate is preferably at least 10 mm, more preferably at least 50 mm.

The process for the cracking reaction is preferably effected at temperatures lower than 300° C. and pressures ranging from 0.2 to 3.0 MPa.

A further object of the present invention relates to the use of the reactor according to the invention for catalytic reactions involving thermal exchanges.

In particular, preferred catalytic reactions involving thermal exchanges which require the use of the reactor according to the invention are etherification reactions between branched olefins and linear alcohol, dimerization reactions of branched olefins and cracking reactions of alkyl ethers.

Preferred embodiments are provided for a better illustration of the present invention, with the help of the enclosed FIGS. 3, 5, 6, 7, 8 and 9 which, however, should not be considered as limiting the scope of the invention itself.

Figure 3:
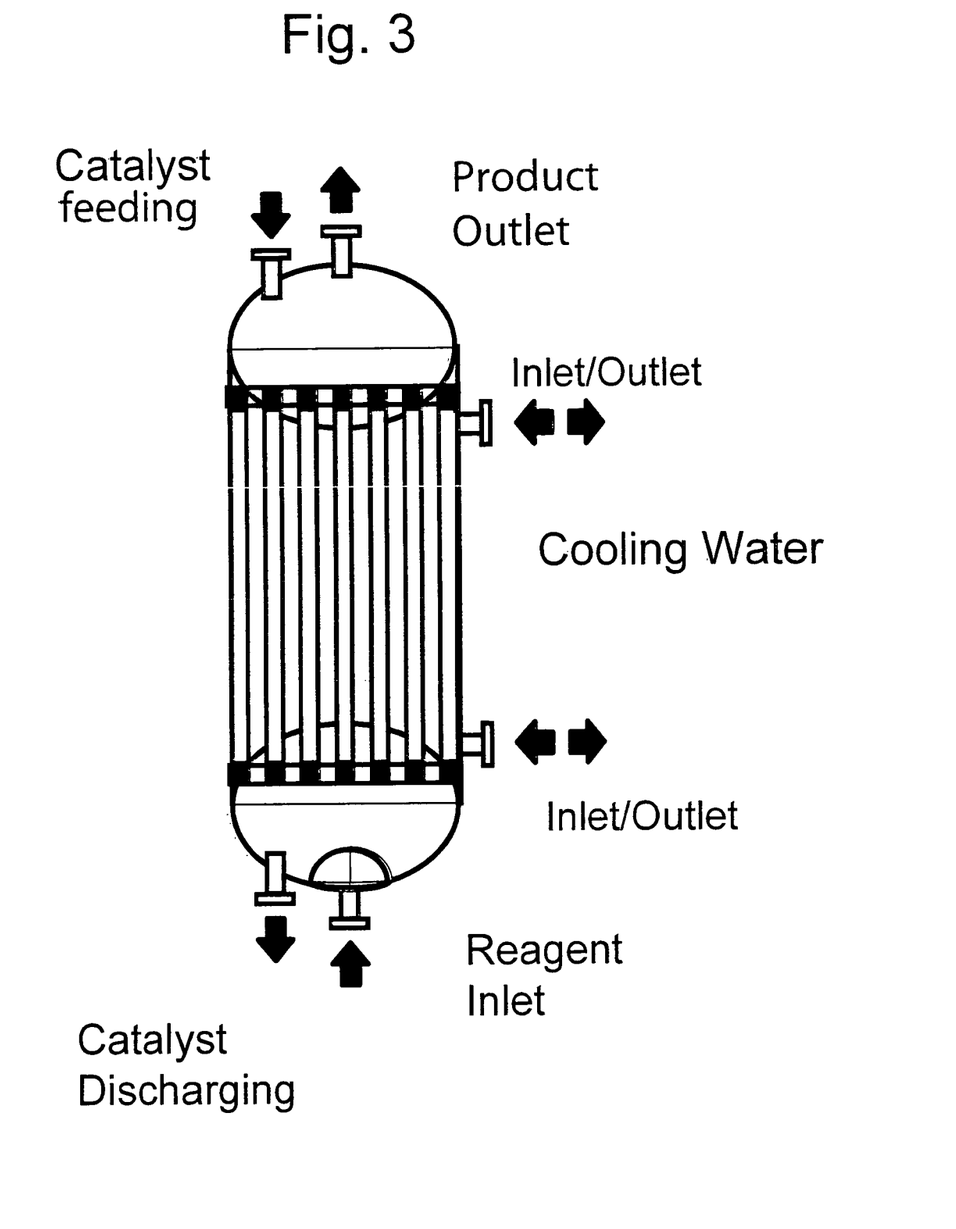
FIG. 3 shows the scheme of the modified tubular reactor.

FIG. 3 shows the scheme of the modified tubular reactor which demonstrates how the catalyst can be easily and rapidly loaded from above and unloaded from the bottom of the reactor analogously to what is effected for an adiabatic reactor. Alternatively, in order to have a better control of the reaction temperature, an inert material can also be used for filling the bottom of the reactor to ensure that the reaction is only initiated in the area in which the thermostat-regulation fluid is present.

In principle, in this reactor configuration, the process fluid can also be fed from above downwards, even if this solution is not recommended as there is a greater possibility of packing of the catalyst.

With this configuration, without support inside the tube plate, the process fluid must obviously be well distributed in the tube bundle and have a maximum rate which is such as to maintain the catalytic bed slightly expanded, avoiding however fluidization and entrainment phenomena of the resin with a consequent emptying of the tubes and the creation of preferential ways.

The rate the fluid must have in the tubes to prevent entrainment depends on the particular geometry of the reactor and is preferably lower than 4.5 cm/sec and more preferably lower than 2.5 cm/sec.

It is therefore extremely important for this invention to have of an efficient distribution system of the process fluid which at the same time does not hinder the discharging operations of the deactivated catalyst.

Figure 4:
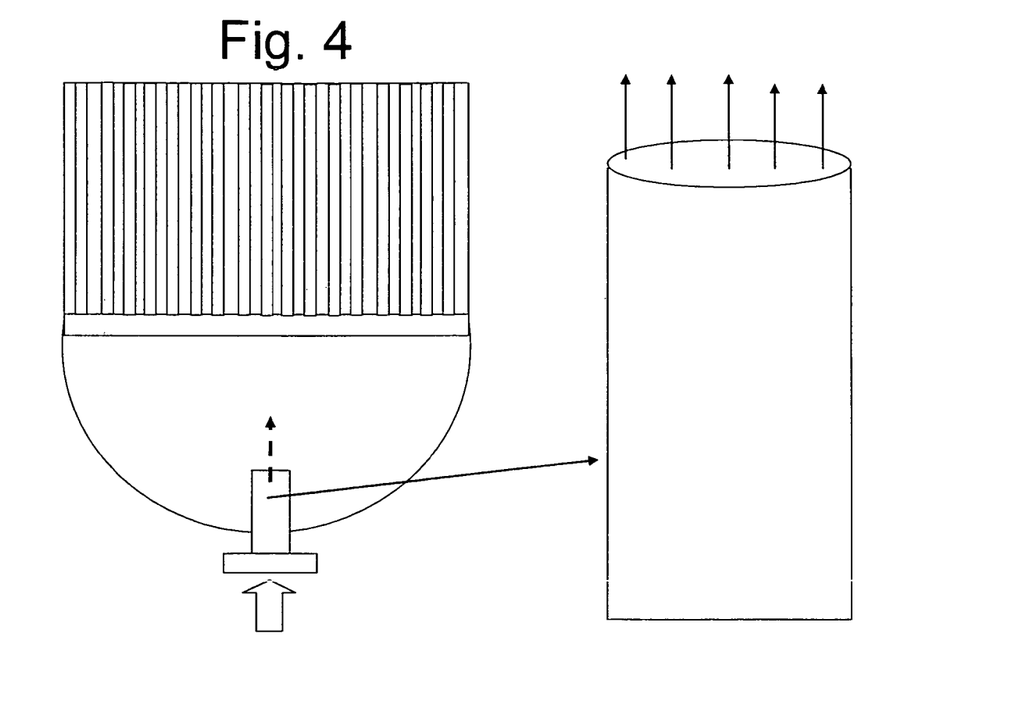
FIG. 4 shows a simplified drawing of the reactor bottom.

In the case of traditional tubular reactors with supports for the catalyst, the distribution of the liquid is effected through a central tube, as shown in FIG. 4, which shows a simplified drawing of the reactor bottom.

This system, however, cannot be used in a modified tubular reactor according to the present invention, with the catalyst in the bottom of the reactor and above the tube plates and device (mesh winding) in the feeding nozzle to withhold the catalyst in the reactor, as the rate of the fluid in the central part of the reactor would be higher than the minimum fluidization rate; new solutions must therefore be found for improving the distribution of the liquid.

Figure 5:
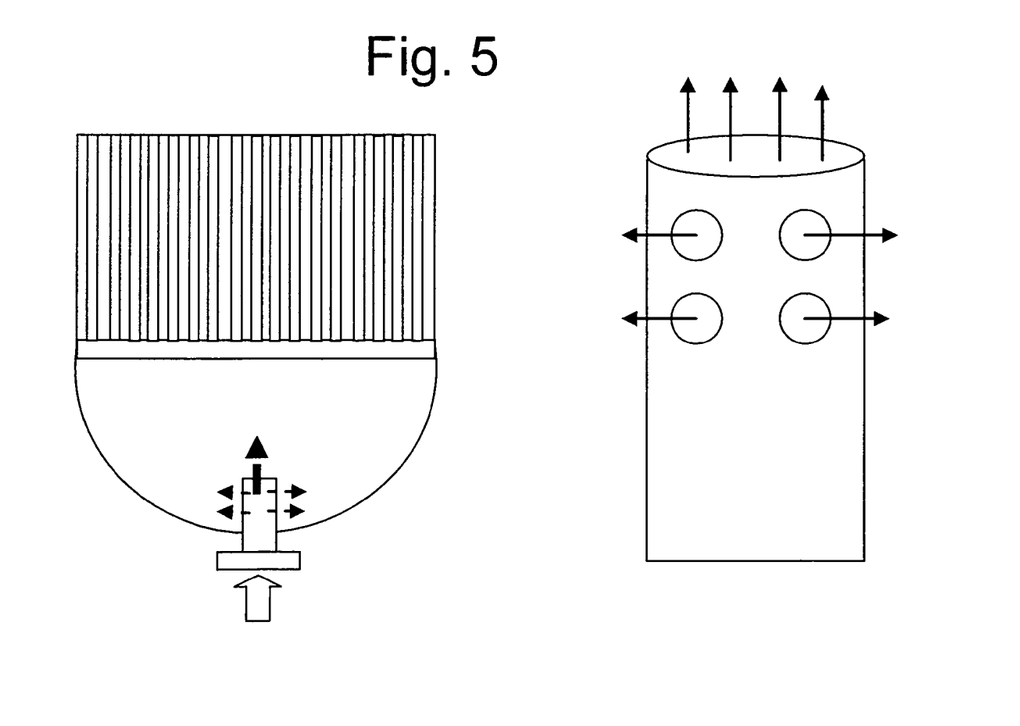
FIG. 5 shows a central distributor, which is substantially a tube, that has been modified by creating a series of circular holes.
Figure 6:
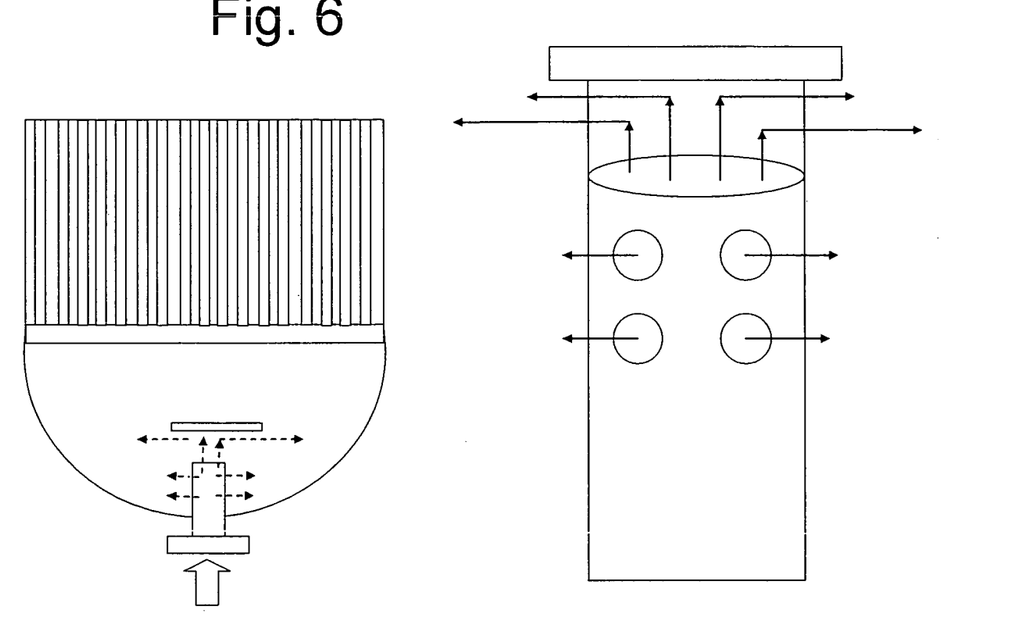
FIG. 6 shows a plate introduced into the distributor, in addition to the side holes, as a deflector, that is positioned at a suitable distance from the central hole.

FIGS. 5 and 6 show two possible modifications of traditional distributors which allow the fluid rate to be reduced in the central area of the reactor.

In FIG. 5 the central distributor, which is substantially a tube, has been modified creating a series of circular holes so as to allow the liquid to also be discharged laterally whereas, in FIG. 6 a plate is also introduced into the distributor, in addition to the side holes, as a deflector, positioned at a suitable distance from the central hole, so as to further reduce the central flow in favour of the side flow. This plate can be completely closed or alternatively equipped with a suitable number of holes.

In the case of new reactors, completely different solutions can be used for the distribution of the process fluid.

Figure 7:
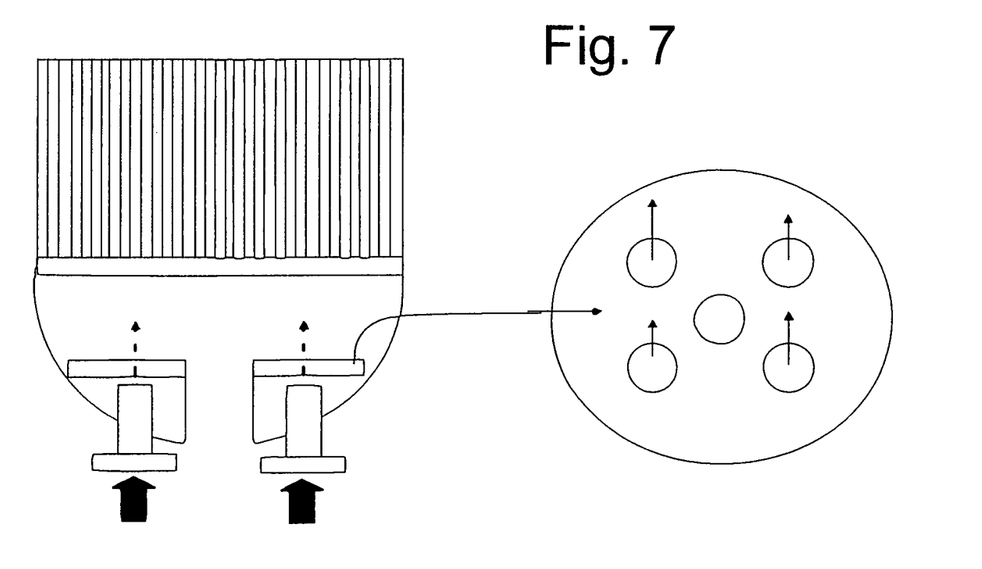
FIG. 7 shows a further possible configuration of the reactor.

FIG. 7 therefore shows a further possible configuration of the reactor which differs from the previous ones in that it does not have a central nozzle for the inlet of the reagents; in this case, the process fluid enters in the bottom of the reactor from at least 2 nozzles situated below a horizontal plate equipped with at least 2 holes, clearly offset with respect to those of the reagent inlet, in addition to a further central hole used exclusively, however, for discharging the deactivated catalyst.

Figure 8:
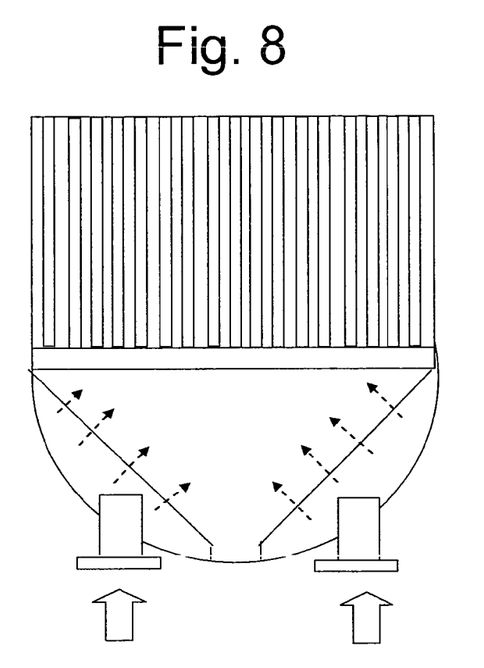
FIG. 8 shows a further possible configuration of the reactor where at least 2 nozzles for feeding the reaction fluid are included.

Alternatively, in the configuration shown in FIG. 8, it is possible to use at least 2 nozzles for feeding the reaction fluid, situated below a tilted perforated plate from whose centre the deactivated catalyst can be recovered. The angulation of this plate preferably ranges from 5 to 80 degrees and more preferably between 10 and 70 degrees.

Figure 9:
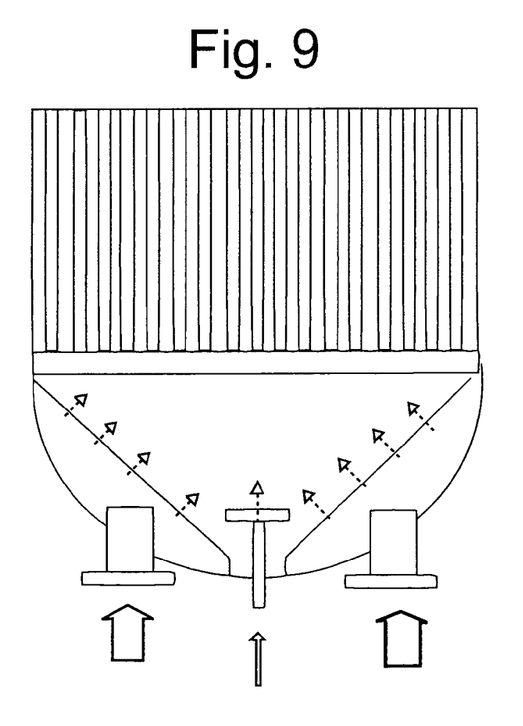
FIG. 9 shows a reactor where, in addition to at least 2 nozzles situated below a tilted perforated plate, the presence of a small central nozzle for the introduction of a part of the process fluid is included.

A further modification of this distribution system, shown in FIG. 9, also envisages, in addition to at least nozzles situated below a tilted perforated plate, the presence of a small central nozzle for the introduction of a part of the process fluid.

The invention claimed is:

1. A tubular reactor, comprising: an upper tube plate present at an upper part of the reactor,
   a lower tube plate present at a lower part of the reactor,
   a vertical tube-bundle exchanger comprising tubes that comprise a catalyst,
   inlet and outlet nozzles for each passage side of the reagents, catalyst and thermal exchange liquid, said nozzles located at the upper and lower parts of the reactor,
   a feeding distributor in communication with the inlet/outlet nozzle located at the lower part of the reactor, and
   at least one metallic support present outside the lower tube plate in the lower part of the reactor for sustaining the catalyst without metallic supporting devices of the catalyst in the tubes,
   wherein said tubular reactor has catalyst present in the tubes, catalyst present in said lower part outside the lower tube plate, and catalyst present in said upper part outside the upper tube plate.

2. The reactor according to claim 1, wherein the metallic support is situated close to or on the lower inlet/outlet nozzle of the reactor.

3. The reactor according to claim 1, wherein the feeding distributor comprises a series of vertical holes, side holes, or a combination thereof.

4. The reactor according to claim 1, wherein a flow deflector is positioned above the distributor.

5. The reactor according to claim 4, wherein the flow deflector is partially perforated.

6. The reactor according to claim 1, further comprising at least two feeding nozzles and at least two feeding distributors, wherein each of the at least two feeding nozzles are in communication with a feeding distributor, equidistant from the vertical axis of the reactor.

7. The reactor according to claim 6, wherein a flow deflector, optionally perforated, is positioned above each distributor in communication with each of the two nozzles.

8. The reactor according to claim 7, wherein the perforated flow deflector positioned above each distributor is tilted.

9. The reactor according to claim 8, wherein the deflector is a perforated plate with an inclination angle ranging from 5 to 80 degrees.

10. The reactor according to claim 9, wherein the inclination angle of the perforated hole ranges from 10 to 70 degrees.

11. The reactor according to claim 8, wherein a further central feeding nozzle of the reagent is present in the bottom of the reactor.

12. The reactor according to claim 1, wherein the reactor is comprised of carbon steel, stainless steel, or a combination thereof.

13. A process, comprising:
    flowing a process fluid comprising reagents for an etherification reaction or a dimerization reaction through the tubular reactor according to claim 1,
    and carrying out said etherification reaction or said dimerization reaction in said tubular reactor.

14. The process according to claim 13, wherein, for catalytic reactions in the liquid phase,
    the process fluid flows upwards;
    a thermostat-regulation fluid flows in the shell side in co-current or countercurrent with respect to the reagents in relation to the quantity of heat to be exchanged; and
    the thermostat-regulation fluid leaving the reactor is brought back to the desired temperature in a suitable external item before being re-circulated into the reactor.

15. The process according to claim 14, wherein said etherification reaction or said dimerization reaction is exothermic.

16. The process according to claim 14, wherein the catalyst comprises a styrene-divinylbenzene polymeric resin having sulfonic groups.

17. The process according to claim 14, wherein linear rates inside the reactor are lower than 4.5 cm/sec.

18. The process according to claim 14, wherein the thermostat-regulation fluid is water.

19. The process according to claim 13, wherein said etherification reaction is a reaction between a branched olefin and a linear alcohol.

20. The process according to claim 19, wherein the etherification reaction is effected at temperatures ranging from 30 to 120° C. and pressures ranging from 0.2 to 3.0 MPa.

21. The process according to claim 19, wherein the linear alcohol is selected from the group consisting of methanol, ethanol, or a mixture thereof.

22. The process according to claim 19, wherein the branched olefin has from 4 to 7 carbon atoms.

23. The process according to claim 13, wherein said dimerization reaction is a dimerization of branched olefins.

24. The process according to claim 23, wherein the dimerization reaction is effected at temperatures ranging from 30 to 120° C. and pressures ranging from 0.2 to 3.0 MPa.

25. The process according to claim 23, wherein the branched olefin has from 4 to 7 carbon atoms.

26. The process according to claim 23, wherein the dimerization reaction is carried out in the presence of a linear alcohol, a branched alcohol, an alkyl ether, or a combination thereof.

27. The process according to claim 26, wherein the alkyl ether is selected from the group consisting of MTBE, ETBE, MSBE, ESBE, TAME, TAEE, and a mixture thereof.

28. The process according to claim 26, wherein the branched alcohol has from 4 to 7 carbon atoms.

29. The process according to claim 26, wherein the linear alcohol is selected from the group consisting of methanol, ethanol, or a mixture thereof.

30. The process according to claim 23, wherein, during said etherification reaction, other olefins optionally present in the feedstock also react to form high-octane products.

31. The process according to claim 19 or 23, wherein the etherification and dimerization reactions of the branched olefins are carried out contemporaneously.

32. A process, comprising:
    flowing a process fluid comprising reagents for a cracking reaction through the tubular reactor according to claim 1,
    and carrying out said cracking reaction in said tubular reactor.

33. The process according to claim 32, wherein reagents for a cracking reaction comprise a branched alcohol having from 3 to 7 carbon atoms.

34. The process according to claim 32, wherein the cracking reaction is carried out at temperatures lower than 300° C. and at pressures ranging from 0.2 to 3.0 MPa.

35. The process according to claim 13 or 32, wherein the minimum height of catalyst above the upper tube plate is at least 10 mm.

36. The process according to claim 35, wherein the minimum height of catalyst above the upper tube plate is at least 50 mm.

37. The process according to claim 13 or 32, wherein the minimum distance of the distributors from the lower tube plate exceeds 10 mm.

38. The reactor according to claim 1, wherein the metallic support is also the feeding distributor.

39. The process according to claim 32, wherein said cracking reaction is a cracking reaction of an alkyl ether.

40. The process according to claim 39, wherein the alkyl ether is selected from the group consisting of MTBE, ETBE, MSBE, ESBE, TAME, TAEE, and a mixture thereof.

41. The process according to claim 31, wherein, for catalytic reactions in the vapor phase,
   the process fluid flows downwards;
   a thermostat-regulation fluid flows in the shell side in equi-current or countercurrent with respect to the reagents in relation to the quantity of heat to be exchanged; and
   the thermostat-regulation fluid leaving the reactor is brought back to the desired temperature in a suitable external item before being re-circulated into the reactor.

42. The process according to claim 41, wherein said cracking reaction is endothermic.

43. The process according to claim 41, wherein the catalyst comprises at least one of a silicon oxide and an aluminum oxide.

44. The process according to claim 41, wherein said thermostat-regulation fluid is steam or hot oil.

* * * * *